US00PP31330P2

(12) United States Plant Patent
Koppe

(10) Patent No.: US PP31,330 P2
(45) Date of Patent: Jan. 7, 2020

(54) ***BEGONIA* PLANT NAMED 'KRELARE02'**

(50) Latin Name: ***Begonia* x *hiemalis***
Varietal Denomination: KRELARE02

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 16/350,336

(22) Filed: Nov. 2, 2018

(51) Int. Cl.
*A01H 5/02* (2018.01)
*A01H 6/18* (2018.01)

(52) U.S. Cl.
USPC ..... Plt./349

(58) Field of Classification Search
USPC ..... Plt./349
CPC ..... A01H 5/02; A01H 5/0238; A01H 5/00; A01H 6/18; A01H 6/32
See application file for complete search history.

(56) References Cited

U.S. PATENT DOCUMENTS

PP9,523 P * 4/1996 Koppe ..... Plt./349

* cited by examiner

*Primary Examiner* — June Hwu
(74) *Attorney, Agent, or Firm* — C. A. Whealy

(57) ABSTRACT

A new and distinct cultivar of *Begonia* plant named 'KRELARE02' characterized by its compact, upright to outwardly spreading and mounded plant habit; moderately vigorous growth habit; freely branching habit; dark green-colored leaves; freely flowering habit; relatively small double-type flowers that are red in color and held above and beyond the foliar plane; and excellent postproduction longevity.

2 Drawing Sheets

Botanical designation: *Begonia* x *hiemalis*.
Cultivar denomination: 'KRELARE02'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRELARE02'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant originated from a cross-pollination made by the Inventor in Ermelo, The Netherlands in January, 2014 of a proprietary selection of *Begonia* x *tuberhybrida* hybrid identified as code number KV10K1804-003, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in June, 2014. Asexual reproduction of the new *Begonia* plant by terminal vegetative cuttings taken in a controlled greenhouse environment in Ermelo, The Netherlands since January, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRELARE02'. These characteristics in combination distinguish 'KRELARE02' as a new and distinct *Begonia* plant:

1. Compact, upright to outwardly spreading and mounded plant habit.
2. Moderately vigorous growth habit.
3. Freely branching habit.
4. Dark green-colored leaves.
5. Freely flowering habit.
6. Relatively small double-type flowers that are red in color and held above and beyond the foliar plane.
7. Excellent postproduction longevity.

Plants of the new *Begonia* differ primarily from plants of the female parent selection in the following characteristics:

1. Plants of the new *Begonia* are more compact than plants of the female parent selection.
2. Plants of the new *Begonia* have smaller flowers than plants of the female parent selection.
3. Plants of the new *Begonia* have double-type flowers whereas plants of the female parent selection have single-type flowers.

Plants of the new *Begonia* differ primarily from plants of the male parent selection in flower color as plants of the male parent selection have pink-colored flowers. In addition, plants of the *Begonia* have double-type flowers whereas plants of the male parent selection have single-type flowers.

Plants of the new *Begonia* can be compared to plants of *Begonia* x *hiemalis* 'Baladin', not patented. In side-by-side comparisons conducted in Ermelo, The Netherlands, plants of the new *Begonia* differ primarily from plants of 'Baladin' in the following characteristics:

1. Plants of the new *Begonia* are more compact than plants of 'Baladin'.
2. Plants of the new *Begonia* have smaller leaves than plants of 'Baladin'.
3. Plants of the new *Begonia* have smaller flowers than plants of 'Baladin'.

Plants of the new *Begonia* can be compared to plants of *Begonia* x *hiemalis* 'Barkos' (U.S. Plant Pat. No. 9,523). In side-by-side comparisons conducted in Ermelo, The Netherlands, plants of the new *Begonia* differ primarily from plants of 'Barkos' in the following characteristics:

1. Plants of the new *Begonia* are more compact than plants of 'Barkos'.
2. Plants of the new *Begonia* have smaller leaves than plants of 'Barkos'.
3. Plants of the new *Begonia* have smaller flowers than plants of 'Barkos'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRELARE02' grown in a container.

The photograph on the second sheet are close up views of the upper (right) and lower (left) surfaces of typical leaves and flowers of 'KRELARE02', and in the center of the photograph is a close-up view of typical flower buds.

DETAILED BOTANICAL DESCRIPTION

The aforementioned photographs and following observations and measurements describe plants grown during the spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were eleven weeks old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRELARE02'.

Parentage:

*Female, or seed, parent*.—Proprietary selection of *Begonia* x *tuberhybrida* hybrid identified as code number KV10K1804-003, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Compact, upright to outwardly spreading and mounded plant habit; overall plant shape, broadly obovate.

*Growth habit*.—Moderately vigorous growth habit and moderate growth rate; suitable for 12-cm and larger containers; under optimal environmental and cultural conditions, usually about nine weeks are required to produce proportional plants in 12-cm containers.

*Branching habit*.—Freely branching with about four primary branches each with about two secondary branches developing per plant.

*Plant height, soil level to top of foliar plane*.—About 25.7 cm.

*Plant height, soil level to top of floral plane*.—About 29.8 cm.

*Plant width*.—About 34.3 cm.

*Lateral branches*.—Length: About 14 cm. Diameter: About 8.5 mm to 10 mm. Internode length: About 2.1 cm. Strength: Moderately strong. Aspect: About 35° from vertical. Texture and luster: Sparsely pubescent; glossy. Color, developing: Close to between 152D and 195A. Color, developed: Close to between 152D and 195A, closest to 195A. Lenticels: Density: Sparse to medium density. Length: About 3 mm. Diameter: About 0.5 mm. Shape: Linear. Color: Close to 145B.

*Leaves*.—Arrangement: Alternate, simple. Length: About 13.2 cm. Width: About 9.3 cm. Shape: Broadly ovate, asymmetrical. Apex: Acute. Base: Hastate with cordate tendencies; lobes slightly imbricate. Margin: Shallowly crenate to dentate; coarsely undulate. Texture and luster, upper surface: Smooth, glabrous; slightly velvety; moderately glossy. Texture and luster, lower surface: Smooth, glabrous; moderately glossy. Venation pattern: Laciniate. Color: Developing leaves, upper surface: Darker than 143A. Developing leaves, lower surface: Close to 138B. Fully expanded leaves, upper surface: Darker than between NN137A and 147A; venation, close to 143B. Fully expanded leaves, lower surface: Close to 191A; at the margins, close to 178B; venation, close to 146D. Petioles: Length: About 4.9 cm. Diameter: About 6 mm. Strength: Low, flexible. Texture and luster, upper and lower surfaces: Sparsely pubescent; moderately glossy. Color, upper surface: Close to N170B tinged with close to 152D; distally, small spot, close to 180A. Color, lower surface: Close to 152D. Stipules: Length: About 1 cm. Width: About 8 mm. Shape: Broadly ovate to roughly deltoid. Apex: Acute. Base: Broadly cuneate. Margin: Irregularly ciliate. Texture and luster, upper and lower surfaces: Smooth, glabrous; moderately glossy. Color, upper and lower surfaces: Close to 145B; apex and margins, tinged with close to 180D; venation, close to 143A.

Flower description:

*Flower appearance and flowering habit.*—Double-type rotate flowers with four tepals and numerous tepaloids; flowers arranged in axillary compound cymes; freely flowering habit with typically about 15 flowers per cyme and about 720 flowers and flower buds developing per plant; many cymes in flower simultaneously; flowers positioned above and beyond the foliar plane and face upright to outwardly; only male flower development has been observed to date on plants of the new *Begonia.*

*Natural flowering season.*—Plants begin flowering about five weeks after planting; plants will flower year round regardless of nyctoperiod, however plants flower earlier and more abundantly from spring into the autumn in The Netherlands.

*Postproduction longevity.*—Individual flowers last about ten days on the plant; flowers not persistent; excellent postproduction longevity, plants maintain good substance for about 40 days in an interior environment.

*Fragrance.*—None detected.

*Inflorescence height.*—About 9.4 cm.

*Inflorescence diameter.*—About 11.3 cm.

*Flowers.*—Shape: Rotate, double-type. Diameter: About 5.2 cm by 5.2 cm. Depth (height): About 2 cm.

*Flower buds.*—Length: About 1.2 cm. Diameter: About 0.5 cm to 1.2 cm. Shape: Broadly ovate to nearly circular, flattened. Texture and luster: Glabrous; slightly velvety; slightly glossy. Color: Close to 45A.

*Tepals.*—Quantity and arrangement per flower: Usually about four per flower arranged in two whorls. Length, lower tepals: About 2.9 cm. Width, lower tepals: About 3.1 cm. Length, upper tepals: About 2.5 cm. Width, upper tepals: About 2.6 cm. Shape, all tepals: Broadly obovate to nearly orbicular. Apex, all tepals: Rounded. Base, all tepals: Reniform. Margin, all tepals: Entire; not undulate. Texture and luster, upper and lower surfaces, all tepals: Smooth, glabrous; moderately velvety; matte. Color, lower tepals: When opening, upper surface: Close to 45B. When opening, lower surface: Close to between 43A and 45B. Fully opened, upper surface: Close to 45C to 45D; towards the margins and apex, close to 45B; venation, similar to lamina color; color does not change with development. Fully opened, lower surface: Close to 46C; venation, close to 45A; color does not change with development. Color, upper tepals: When opening, upper surface: Close to 45B. When opening, lower surface: Close to between 45B and 45C. Fully opened, upper surface: Close to 45C; towards the margins and apex, close to 46C; venation, similar to lamina color; color does not change with development. Fully opened, lower surface: Close to 46C; venation, close to 45A; color does not change with development.

*Tepaloids.*—Quantity and arrangement per flower: Typically about 15 per flower clustered at the center of the flower. Length: About 0.8 cm to 2.1 cm. Width: About 0.3 cm to 1.7 cm. Shape: Obovate. Apex: Obtuse to broadly and bluntly acute. Base: Attenuate. Margin: Entire; not undulate. Texture and luster, upper and lower surfaces: Smooth, glabrous; moderately velvety; matte. Color: When opening, upper surface: Close to 45B. When opening, lower surface: Close to N45C. Fully opened, upper surface: Close to 46C; venation, similar to lamina color; color does not change with development. Fully opened, lower surface: Close to 46C; venation, close to N45B; color does not change with development.

*Peduncles.*—Length: About 7.1 cm. Diameter: About 4 mm to 5 mm. Strength: Moderately strong. Aspect: About 25° from lateral branch axis. Texture and luster: Smooth, glabrous; moderately glossy. Color: Close to N199C tinged with close to 152A.

*Pedicels.*—Length: About 2.8 cm. Diameter: About 2 mm. Strength: Moderately strong. Aspect: About 20° from peduncle axis. Texture and luster: Smooth, glabrous; glossy. Color: Close to 179B.

*Flower bracts.*—Quantity per flower: Two. Length: About 1.6 cm. Width: About 1.4 cm. Shape: Broadly ovate. Apex: Broadly acute. Base: Broadly cuneate. Margin: Ciliate. Texture and luster, upper and lower surfaces: Smooth, glabrous; slightly glossy. Color, upper surface: Close to 185A and 187A; towards the base, close to 146D. Color, lower surface: Close to 179A and 185A; towards the base, close to 146D.

*Reproductive organs.*—Stamens transformed into tepaloids; flowers are sterile. Female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRELARE02' as illustrated and described.

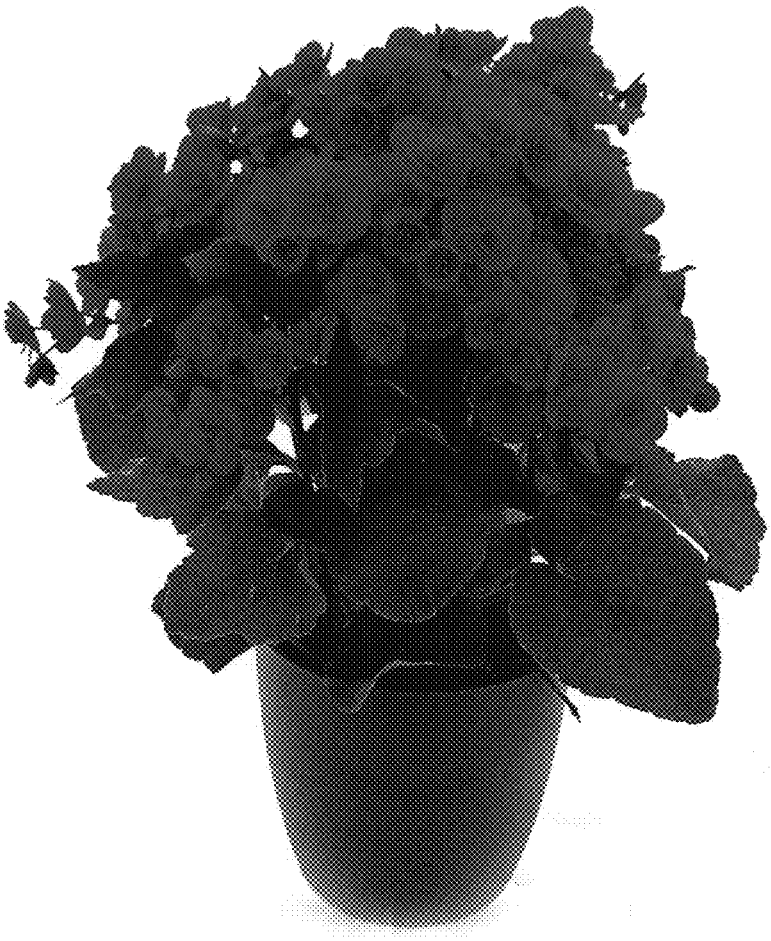

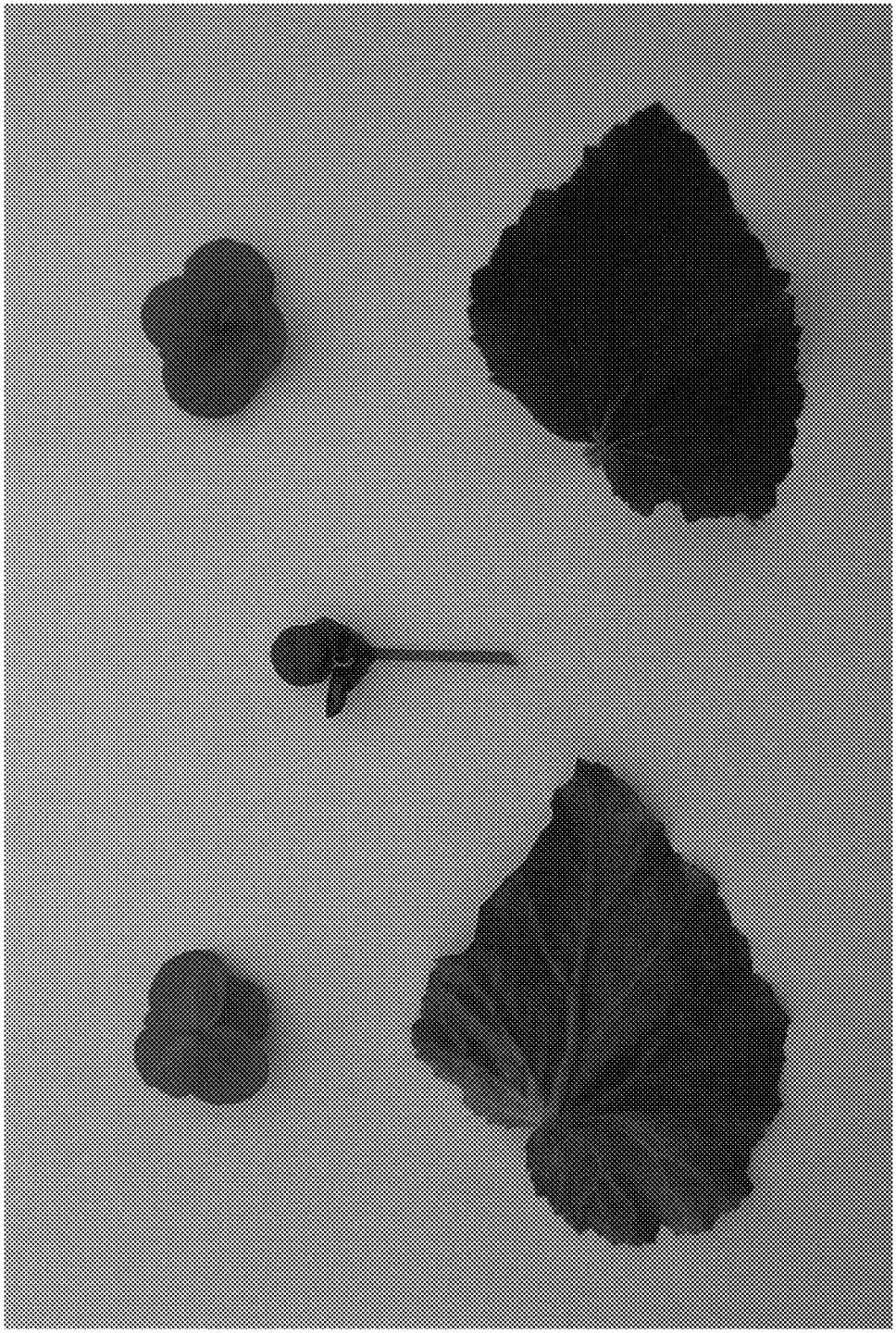

* * * * *